(12) United States Patent
Romano (10) Patent No.: US 12,285,567 B2
(45) Date of Patent: Apr. 29, 2025

(54) HIGH FLOW OXYGEN THERAPY WITH ON-DEMAND HUMIDIFICATION AND AN ACTIVE EXHALATION VALVE

(71) Applicant: KONINKLIJKE PHILIPS N.V., Eindhoven (NL)

(72) Inventor: Robert Romano, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 263 days.

(21) Appl. No.: 16/468,428

(22) PCT Filed: Dec. 13, 2017

(86) PCT No.: PCT/EP2017/082621
§ 371 (c)(1),
(2) Date: Jun. 11, 2019

(87) PCT Pub. No.: WO2018/109006
PCT Pub. Date: Jun. 21, 2018

(65) Prior Publication Data
US 2021/0213234 A1    Jul. 15, 2021

Related U.S. Application Data

(60) Provisional application No. 62/433,872, filed on Dec. 14, 2016.

(51) Int. Cl.
*A61M 16/10* (2006.01)
*A61M 16/20* (2006.01)

(52) U.S. Cl.
CPC ........ *A61M 16/101* (2014.02); *A61M 16/205* (2014.02); *A61M 2016/102* (2013.01)

(58) Field of Classification Search
CPC .............. A61M 16/101; A61M 16/205; A61M 2016/102
See application file for complete search history.

(56) References Cited

U.S. PATENT DOCUMENTS

| | | | |
|---|---|---|---|
| 8,074,645 | B2 | 12/2011 | Bordewick et al. |
| 8,307,825 | B1 | 11/2012 | Roberts |

(Continued)

FOREIGN PATENT DOCUMENTS

| | | | | |
|---|---|---|---|---|
| CA | 2886596 | A1 * | 4/2014 | ........ A61M 16/0003 |
| CN | 201643291 | U * | 11/2010 | |

OTHER PUBLICATIONS

G-B Jin and et al, "Design and experiments of extrusion die for polypropylene five-lumen micro tube", Journal of Materials Processing Technology 214 (2014) 50-59 (Year: 2014).*

(Continued)

*Primary Examiner* — Douglas Kay
(74) *Attorney, Agent, or Firm* — Michael W. Haas (57) ABSTRACT

The present disclosure pertains to a system for delivering a humidified flow of concentrated oxygen containing gas to a subject, the system comprising: a subject interface; an oxygen concentrator operatively coupled to the subject interface, the oxygen concentrator configured to provide a flow of concentrated oxygen containing gas to the subject interface via a first conduit; and an aerosol generator operatively coupled to a water supply via a second conduit, the aerosol generator configured to provide a water vapor to the subject interface via the second conduit to humidify the flow of concentrated oxygen containing gas for delivery to the subject.

10 Claims, 6 Drawing Sheets

(56) References Cited

U.S. PATENT DOCUMENTS

| | | | |
|---|---|---|---|
| 8,839,791 B2 | 9/2014 | Allum et al. | |
| 9,399,109 B2* | 7/2016 | Baloa Welzien | A61M 16/201 |
| 10,086,158 B2* | 10/2018 | Bath | A61M 16/065 |
| 2006/0201504 A1 | 9/2006 | Singhal et al. | |
| 2007/0137646 A1* | 6/2007 | Weinstein | A62B 9/003 |
| | | | 128/204.17 |
| 2007/0246049 A1 | 10/2007 | Takeda et al. | |
| 2008/0072903 A1* | 3/2008 | Roth | A61M 16/1095 |
| | | | 128/204.22 |
| 2009/0050153 A1 | 2/2009 | Brunner | |
| 2010/0071693 A1* | 3/2010 | Allum | A61M 16/0465 |
| | | | 128/205.24 |
| 2010/0282247 A1* | 11/2010 | Kadrichu | A61M 15/0086 |
| | | | 128/200.14 |
| 2012/0138050 A1* | 6/2012 | Wondka | A61M 16/0057 |
| | | | 128/203.14 |
| 2013/0087143 A1 | 4/2013 | Pujol | |
| 2013/0228181 A1* | 9/2013 | Ahmad | A61M 16/0069 |
| | | | 128/204.23 |
| 2013/0327323 A1 | 12/2013 | Rubin | |
| 2014/0158123 A1* | 6/2014 | Mazela | A61M 16/14 |
| | | | 128/203.12 |
| 2014/0251331 A1* | 9/2014 | Korneff | A61M 16/0875 |
| | | | 128/203.27 |
| 2015/0165146 A1 | 6/2015 | Bowman | |
| 2016/0206768 A1* | 7/2016 | Mullins | A01N 59/12 |
| 2016/0216712 A1* | 7/2016 | Baumgartner | A61L 9/122 |
| 2016/0303340 A1* | 10/2016 | Sinderby | A61M 16/20 |
| 2017/0182266 A1* | 6/2017 | Power | A61M 16/024 |
| 2017/0216552 A1* | 8/2017 | Goff | A61M 16/109 |

OTHER PUBLICATIONS

L. Papazian and et al, "Use of high-flow nasal cannula oxygenation in ICU adults: a narrative review", Intensive Care Medicine vol. 42, pp. 1336-1349 (2016), Published: Mar. 11, 2016 (Year: 2016).*

S. Sangwan and et al, "Facemasks and facial deposition of aerosols", Pediatric Pulmonology, vol. 37, Issue May 5, 2004, p. 447-452 (Year: 2004).*

I. Amirav and et al, "Nebuliser hood compared to mask in wheezy infants: aerosol therapy without tears!", Arch Dis Child 2003;88: 719-723 (Year: 2003).*

C. C. White and et al, "Bronchodilator Delivery During Simulated Pediatric Noninvasive Ventilation", Respiratory Care • Sep. 2013 vol. 58 No. 9 (Year: 2013).*

* cited by examiner

FIG. 1

Show with leur fitting

Patient interfaces shown with tubing connections

```
┌─────────────────────────────────────┐
│ Provide a flow of concentrated oxygen│──402
│ containing gas to the subject interface│
└─────────────────────────────────────┘
                  │
┌─────────────────────────────────────┐
│ Provide a water vapor to the subject │──404
│ interface with an aerosol generator  │
└─────────────────────────────────────┘
                  │
┌─────────────────────────────────────┐
│        Generate output signals       │──406
└─────────────────────────────────────┘
                  │
┌─────────────────────────────────────┐
│  Activate the aerosol generator based│──408
│        on the output signals         │
└─────────────────────────────────────┘
                  │
┌─────────────────────────────────────┐
│ De-activate the aerosol generator    │──410
│    based on the output signals       │
└─────────────────────────────────────┘
```

FIG. 4

100 # HIGH FLOW OXYGEN THERAPY WITH ON-DEMAND HUMIDIFICATION AND AN ACTIVE EXHALATION VALVE

CROSS-REFERENCE TO PRIOR APPLICATIONS

This application is the U.S. National Phase application under 35 U.S.C. § 371 of International Application Serial No. PCT/EP2017/082621, filed on 13 Dec. 2017, which claims the benefit of U.S. application Ser. No. 62/433,872, filed on 14 Dec. 2016. These applications are hereby incorporated by reference herein.

BACKGROUND OF THE INVENTION

1. Field of the Invention

The present disclosure pertains to a system and method for delivering a humidified flow of concentrated oxygen containing gas to a subject.

2. Description of the Related Art

Subjects with some respiratory diseases, particularly, Chronic Obstructive Pulmonary Disease (COPD) often require oxygen therapy to help increase the concentration of oxygen in the blood. Studies have found that additional improvements in blood oxygenation can be achieved when oxygen/air mixture is delivered at high flow rates (e.g., up to 60 L/min). This high flow rate of gas, when delivered to the subject through an appropriate therapy interface at a constant flow rate during the breath cycle, creates a positive pressure of several centimeters H₂O during expiration. However, in some cases, these high flows rates can be uncomfortable for the subject due to excessive drying of the oro-nasal and upper airways. In addition, some COPD subjects suffer from Expiratory Flow Limitation (EFL). Expiratory Flow Limitation is a physiological condition where a person's airways lose their elastic recoil due to parenchymal destruction which causes the airways to partially collapse during expiration. Generally, to treat expiratory flow limitation, some form of backpressure during expiration is provided in order to splint open the airways and improve ventilation. Current methods designed to supply high flow oxygen to subjects have several disadvantages. For example, systems used to deliver humidity to the oxygen/air gas mixture require large and often bulky humidification systems. This invention overcomes deficiencies in prior art systems.

SUMMARY OF THE INVENTION

Accordingly, one or more aspects of the present disclosure relate to a system for delivering a humidified flow of concentrated oxygen containing gas to a subject, the system comprising: a subject interface; an oxygen concentrator operatively coupled to the subject interface, the oxygen concentrator configured to provide a flow of concentrated oxygen containing gas to the subject interface via a first conduit; and an aerosol generator operatively coupled to a water supply via a second conduit, the aerosol generator configured to provide a water vapor to the subject interface via the second conduit to humidify the flow of concentrated oxygen containing gas for delivery to the subject.

Another aspect of the present disclosure relates to a method for delivering a humidified flow of concentrated oxygen containing gas to a subject, the method comprising: providing, with an oxygen concentrator operatively coupled to a subject interface, a flow of concentrated oxygen containing gas to the subject interface via a first conduit; and providing, with an aerosol generator operatively coupled to a water supply via a second conduit, a water vapor to the subject interface via the second conduit to humidify the flow of concentrated oxygen containing gas for delivery to the subject.

Still another aspect of present disclosure relates to a system for delivering a humidified flow of concentrated oxygen containing gas to a subject, the system comprising: means for providing a flow of concentrated oxygen containing gas to a subject interface via a first conduit, the means for providing the flow being operatively coupled to the subject interface via the first conduit; and means for providing a water vapor to the subject interface via a second conduit to humidify the flow of concentrated oxygen containing gas for delivery to the subject, the means for providing the water vapor being operatively coupled to a water supply via the second conduit.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

To mitigate some or all of the issues described above, the present system (shown in FIG. 1 and FIG. 2 and described in detail below) includes a humidifier configured to nebulize or aerosolize water drops into a small particulate size and deliver the water vapor proximal to the subjects' oro-nasal region. Advantageously, this eliminates the need for a heated tube because it reduces the possibility of the condition known as "rain-out" where the water vapor condenses along the sides of the tube. To provide positive pressure during expiration, the present system uses an exhalation valve (e.g., an active exhalation valve), proximal to the subject's oro-nasal region to allow for increased control of the expiratory pressure and decrease any $CO_2$ rebreathing. An active exhalation valve may have the advantage of allowing for a relatively small diameter tube to be used between the gas source and subject interface. Thus, if used with a portable oxygen concentrator, a smaller compressor size and less energy would be required.

Figure 1:
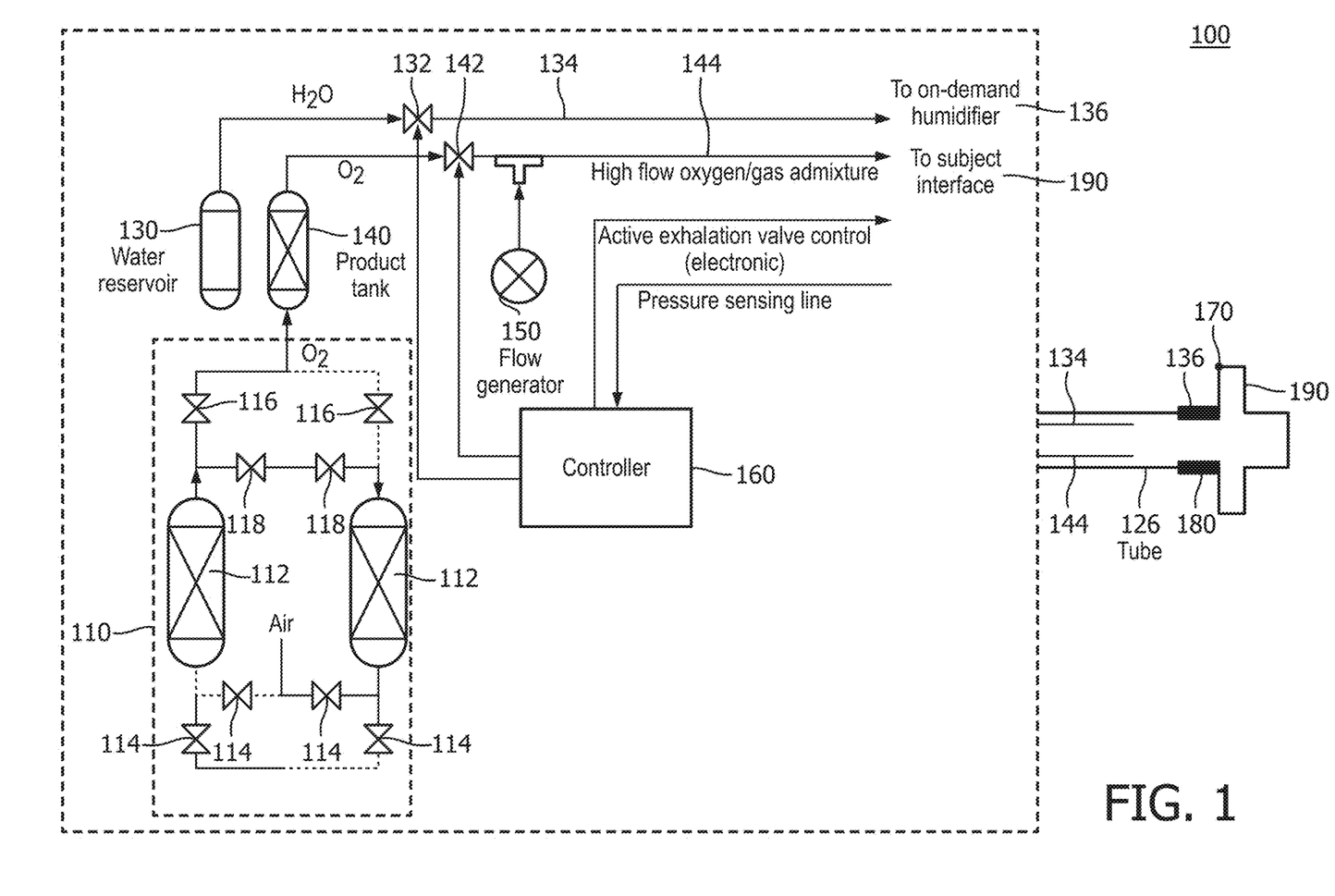
FIG. 1 is a schematic illustration of a system for delivering a humidified flow of concentrated oxygen containing gas to a subject in accordance with one or more implementations.
Figure 2:
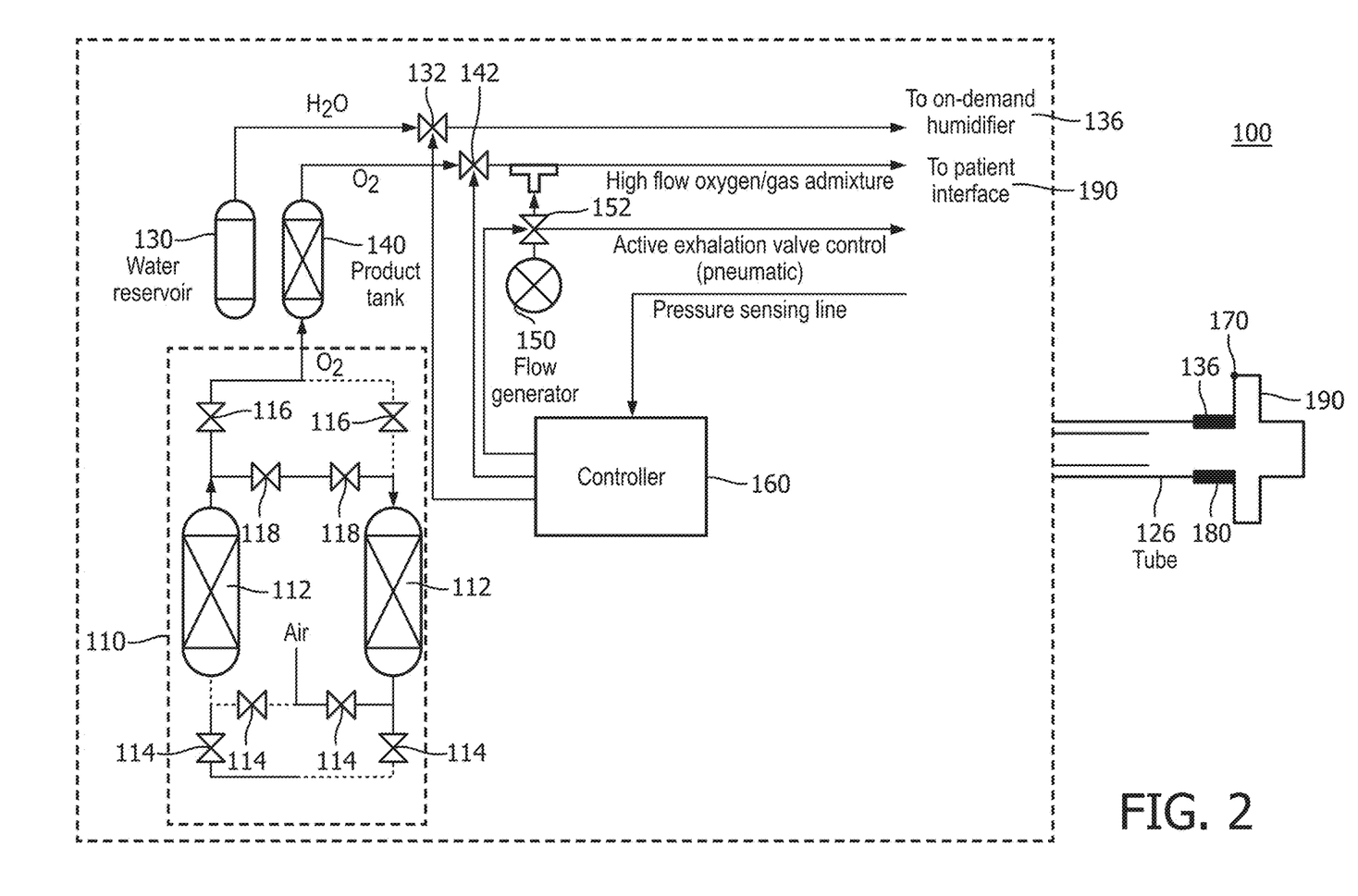
FIG. 2 is a schematic illustration of a system for delivering a humidified flow of concentrated oxygen containing gas to a subject in accordance with one or more implementations.

FIGS. 1 and 2 are schematic illustrations of a system 100 configured to deliver a humidified flow of concentrated oxygen containing gas to a subject. System 100 overcomes some or all the shortcomings of existing systems described above. For example, subjects with pulmonary or cardiac disease usually feel a shortness of breath upon exertion or exercise. Some of these subjects are prescribed oxygen to help prevent them from oxygen desaturation. For those subjects already using an oxygen delivery system and nasal cannula, system 100 may replace their existing oxygen system and nasal cannula. This would provide additional relief during exertion, allowing them to increase their physical activity and improve their quality of life. For less demanding situations, some subjects may use system 100 in a similar manner that they use their conventional oxygen cannula and $O_2$ delivery system. The components of system 100 integrated together provide for a relatively small and portable solution for the delivery of high flow oxygen/gas admixture to a subject with an increase in humidity with positive expiratory pressure and allow for a relatively small diameter gas delivery tube.

In some embodiments, system 100 comprises a breathable gas source 120 operatively connected to subject interface 190 via tube 126. In some embodiments, a humidifier 136 is provided proximal to subject interface 190. In some embodiments, an exhalation valve 170, and one or more sensors 180 are provided proximal to subject interface 190. In some embodiments, system 100 may provide a portable, relatively small and light (e.g., compared to existing systems) system for the delivery of high flow oxygen/gas admixture to a subject with increase on humidity, positive expiratory pressure, and a relatively small diameter gas delivery tube 126. For example, in some embodiments, during the inspiration cycle, an oxygen/gas admixture is delivered to the subject at flow rates in excess of 40 L/min (e.g., between about 30 and 220 L/min), through tube 126 having a relatively small internal diameter (e.g., 8 mm). Upon sensing the start of expiration (e.g., using sensors 180), a controller switches off the flow of oxygen and activate exhalation valve 170 to allow for the exhaust of expired gas to ambient air. In some embodiments, exhalation valve 170 may be a control valve configured to regulate the positive expiratory pressure either by orifices or by controlling the degree by which the valve is allowed to be open. In some embodiments, the humidifier 136 may be controlled such that humidifier 136 is turned ON during the inspiration cycle of a breath and turned OFF during exhalation. In some cases, water may be delivered to humidifier 136 through a capillary tube.

Figure 1A:
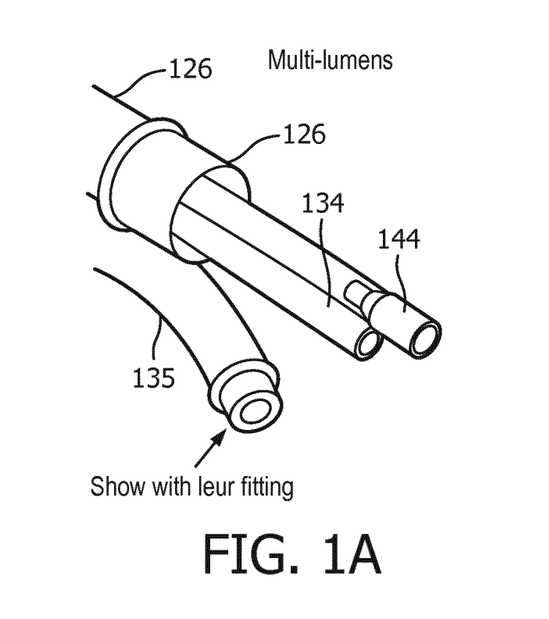
FIGS. 1A-D show multiple examples of subject interface and tubing in accordance with one or more implementations.
Figure 1B:
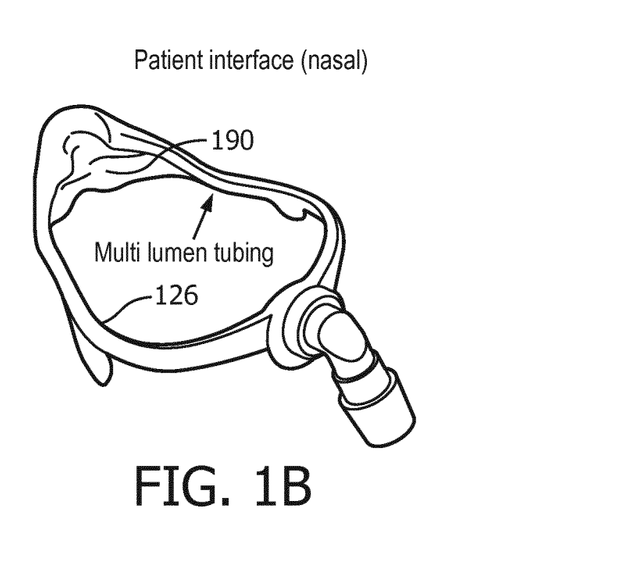
Figure 1C:
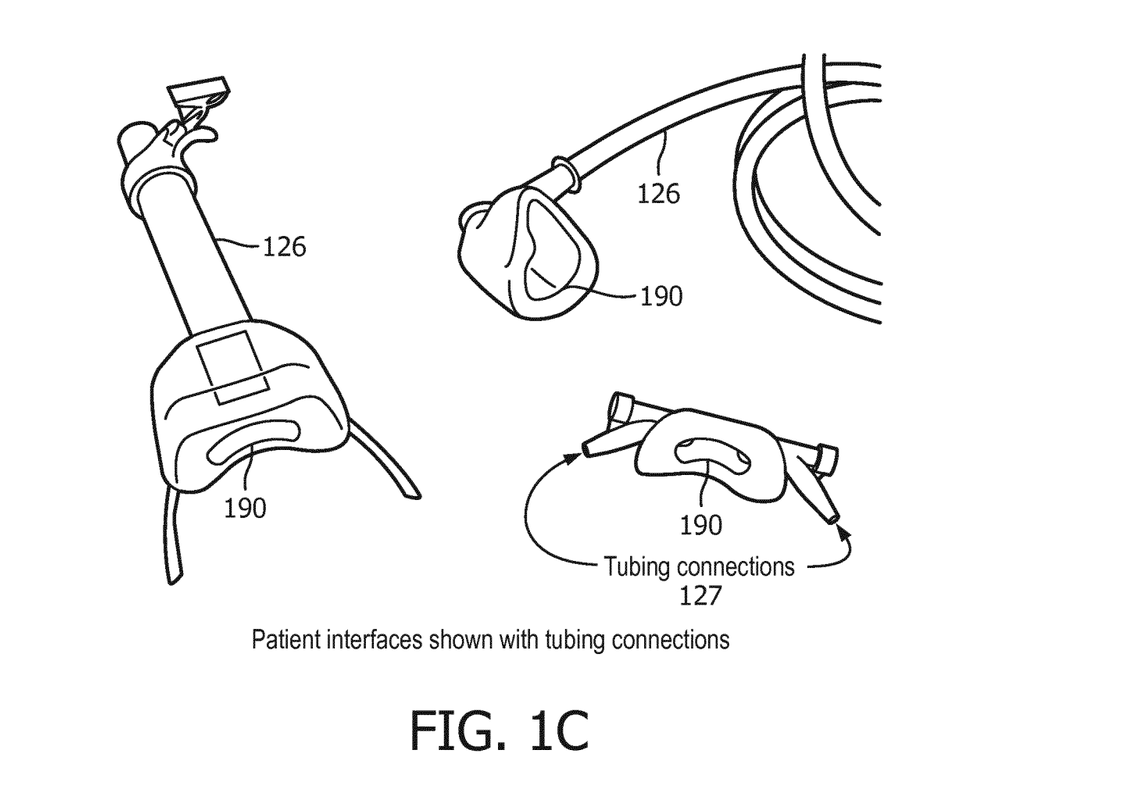
Figure 1D:
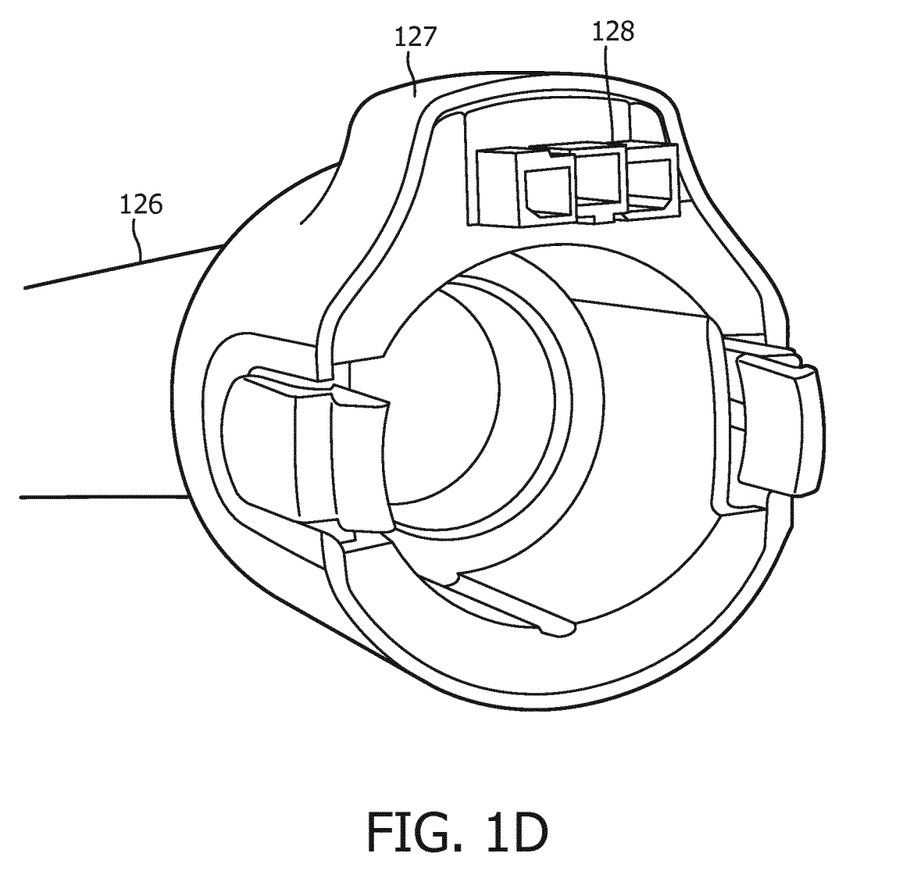

In some embodiments, tube 126 is a multi-limb system that includes for example, one or more of an inspiratory limb to deliver a flow of gas to the subject, an expiratory limb to communicate a flow of expiratory gas from the subject, a limb for water delivery, and/or a limb for medication delivery. In some embodiments, tube 126 includes a multi-lumen portion including one or more delivery conduits (e.g., tube 126 may be a multi-lumen tube in its entirety, or just a portion of tube 126 is a multi-lumen tube). In some embodiments, tube 126 may be a combination of multi-lumen and multi-limb tubing. For example FIG. 1A shows a tube 126 that includes a multi lumen portion (including breathable gas conduit 144 and water conduit 134) and a separate limb 135. In some embodiments, the multi-lumen portion includes one or more conduits operatively connected to subject interface 190 (e.g., at connections 127 shown in FIG. 1C). In some embodiments, connection 127 may include an electrical connector 128 (Shown in FIG. 1 D) configured to provide an electrical connection to one or more components of system 100 (e.g., sensors 180, humidifier 136, valve 170, subject interface 190, and/or other components).

In some embodiments the multi-lumen portion includes one or more breathable gas conduits (e.g., operatively connected to source of breathable gas and), one or more of a water conduits (e.g., operatively connected to water reservoir and to the humidifier and/or subject interface), a medication conduit (operatively connected to source of medication and subject interface), and/or other conduits for delivery to subject interface 190. FIGS. 1 and 2 show an example multi-lumen tube 126 including a first breathable gas conduit 144 and a second water conduit 134. FIGS. 1A-C show multiple examples of subject interface 190 and/or multi-lumen tube 126 in accordance with one or more embodiments.

A small diameter tube 126 may be used to deliver high flow breathable gas (in part because of exhalation valve 175 which provides positive expiratory pressure). In some embodiments, tube 126 may have an internal dimeter of less than 22 mm, less than 15 mm, or less than 8 mm. However, it is to be understood that a conventional size tube 126 may be used and is consistent with the embodiments of the invention.

In some embodiments, the breathable gas source comprises one or more of an oxygen concentrator 110, a water reservoir 130, a water valve 132, a product tank 140, a gas valve 142, a flow generator 150, a controller 160, and or other components.

In some embodiments, concentrator 110 is operatively coupled to the subject interface, and configured to provide a flow of breathable gas (e.g., concentrated oxygen containing gas) to the subject interface via a first conduit 144. In some embodiments, concentrator 110 may include a plurality of sieve beds 112 (e.g., tanks or other beds) for concentrating oxygen from ambient air by adsorption within the sieves. Concentrator 110 may include one or more additional components. For example, in some embodiments, concentrator 110 may include a compressor (not shown) configured to draw ambient air into the oxygen concentrator 110 and compressing the air to one or more desired pressures for delivery to sieve beds 112.

In some embodiments, concentrator 110 may include a plurality of valves 114 (e.g., air control valves) for controlling airflow in and out of concentrator 110 (e.g., from an air inlet to sieve beds 112, or from a compressor outlet to sieve beds 112, between sieve beds, or from sieve beds 112 to an exhaust, etc.). Valves 114 may allow each sieve bed 112 to be pressurized and/or exhausted independently of the other, and in some cases allow overlapping of the pressurization cycles of the sieve beds. Valves 114 may be one or more of two-way valves, three-way valves, or other multiple position valves. In some embodiments, operations of valves 114 (opening, closing, or degree of opening and closing, etc.) may be controlled by controller 160 (described below).

In some embodiments, concentrator 110 may include a plurality of check valves 116 for providing one-way flow paths from sieve beds 112 to product tank 140. Valves 116 may be check valves that open in one direction depending upon the pressure differential across the valve. In some cases, a pressure sensor may be provided to measure pressure within the product tank 140, within oxygen delivery line between a sieve bed 112 and product tank 140, and/or within sieve beds 112. The pressure sensor may be located in the oxygen delivery line, in product tank 140, or in other locations within or outside concentrator 100. In some embodiments, in operation, a check valve 116 allows one-way flow of oxygen from sieve beds 112 into oxygen delivery line and into the product tank 140, such that whenever the pressure in either sieve bed 112 exceeds the pressure in the product tank 140, the respective check valve 116 may open, and once the pressure within either sieve bed 112 becomes equal to or less than the pressure in product tank 140, the respective check valve 116 may close. In some embodiments, valves 116 may be pressure-activated valves, spring biased valves, umbrella-type valves, or other types of valves.

In some embodiments, concentrator 110 may include valves 118 for providing a flow path for oxygen from one sieve bed 112 to another sieve bed 112, e.g., while the one sieve bed is charging and the other is purging. In some embodiments, valves 118 may remain open or open and close based on the pressure cycle of the sieve beds in order to control pressurization or purging of the sieve beds 112. In some cases, degree of opening of valves 118 may be based on flow (e.g., to allow for a predetermined flow rate of oxygen). Operations of valves 118 may be controlled by controller 160 or a controller within concentrator 110 in some embodiments.

In operation, in some embodiments, sieve beds 112 are charged and purged alternatively such that when a sieve bed 112 is being charged or pressurized, ambient air is delivered to the sieve bed (e.g., air compressed with a compressor, in some cases). Nitrogen is substantially adsorbed by the sieve material in the sieve bed, as sieve bed 112 is being pressurized, and oxygen escapes through the oxygen inlet/outlet of sieve bed 112, where it may be stored in reservoir 140 and/or be delivered to the user. Once the pressure within sieve bed 112 reaches a predetermined limit (or after a predetermined time), sieve bed 112 may then be purged (e.g., by exposing the air inlet/outlet end to ambient pressure). This causes the compressed nitrogen within sieve bed 112 to escape through air valves 114 for example. Optionally, as sieve bed 112 is being purged, oxygen escaping from the other sieve bed 112 (which may be being charged simultaneously) may pass through valves 118 into the oxygen inlet/outlet end of the purging sieve bed 112, e.g., if the pressure within the charging sieve bed is greater than within the purging sieve bed, which may occur towards the end of purging. In addition and/or alternatively, oxygen may pass through the check valves 116 between the sieve beds, e.g., when the relative pressures of the sieve beds 112 and the reservoir 140 causes the check valves 116 to open, in addition to or instead of through valves 118. This oxygen delivery into the oxygen inlet/outlet end of the sieve bed 112 being purged may assist in evacuating the concentrated nitrogen out of the sieve bed 112 before it is charged again.

In some embodiments, product tank 140 is a reservoir configured to store breathable gas and/or deliver it to the subject. Product tank 140 may be in direct communication with concentrator 110 (e.g., via an oxygen line). In some embodiments, in addition to the oxygen line (delivering concentrated oxygen from concentrator 110), product tank 140 may be connected to another source of breathable gas (oxygen or other breathable gas) such that an admixture of oxygen from oxygen concentrator and breathable gas from the other source is stored in tank 140 and/or delivered to the subject. In some embodiments, system 100 does not include concentrator 110. For example, product tank 140 may be configured to couple directly to a source of breathable gas (e.g., within or outside of system 100).

In some embodiments, system 100 may include a plurality of tanks or reservoirs 140 in one or more locations in system 100. For example, the reservoirs may be coupled together via tubes to allow the breathable gas to be delivered to and withdrawn from the reservoirs. In some embodiments, one or more valves may be used to control flow of breathable gas into, out of, and between the reservoirs. For example, some reservoirs may be coupled to the concentrator while other reservoirs are supplementing either a different breathable gas or a supplement of concentrated oxygen for an admixture in one of the reservoirs for the breathable gas delivery to the subject. In this embodiment, valves may be used to control which reservoir and when an individual reservoir is used.

In some embodiments, the breathable gas is directed from product tank 140 to a flow generator 150. A gas valve 142 may be used between the product tank 140 and flow generator 150. Valve 142 may be configured to control pressure and/or flow of the breathable gas downstream from product tank 140. In embodiments where system 100 does not include a product tank 140, valve 142 controls flow of the breathable gas downstream from the source of the breathable gas. In some embodiments, valve 142 may be configured to control the pressure and/or flow of the breathable gas by exhausting gas from the gas line to atmosphere and restricting the flow of the breathable gas to the subject. Examples of such control valves may include sleeve and/or poppet valves, and/or other valves. In some embodiments, control of the pressure and/or flow of the breathable gas may be done by controlling the position of valve 142 (e.g., open, close, degree by which the valve is open, degree by which the valve is closed, etc.).

In some embodiments, controller 160 controls operations of control valve 142. For example, the control is based on measured pressure and/or flow (from information in output signals generated by sensor 180) within one or more components of system 100 (e.g., product tank 140, tube 126, subject interface 190, etc.). Signals from a flow/pressure sensor 180 may be used to monitor flow of the oxygen containing gas in the subject circuit (126, 190). The signal from flow sensor 180 is used to control opening and closing of gas valve 142 to deliver the oxygen containing gas from product tank 140 to the subject (e.g., if system 100 is operating to supply a continuous flow of oxygen). In some embodiments, flow/pressure sensor 180 may be used to monitor flow of the oxygen containing gas flowing through subject circuit (126, 190). The pressure differential signal from pressure sensor 180 is used to control opening and closing gas valve 142 to deliver the oxygen containing gas from product tank 140 to the subject (e.g., if system 100 is operating in pulse delivery where oxygen is supplied in predetermined pulses).

In some embodiments, control valve 142 may be controlled alone or in concert with other components of system 100 to provide a controlled pressure and/or flow of breathable gas to the subject. For example, in some cases, valve 142 and flow generator 150 (described in detail below) may operate together to provide a desirable pressure and/or flow rate of the breathable gas by adjusting operating parameters of flow generator 150, and adjusting control settings associated with control valve 142 so that the two, operating together, determine the final pressure and/or flow rate for the breathable gas. In some embodiments, valve 142 is incorporated in flow generator 150 and may be used to determine the flow of breathable gas in subject circuit (126, 190) (e.g., position of the valve, in flow generator 150 corresponds to the flow of gas in the subject circuit). In other embodiments, system 100 does not include control valve 142, and control of pressure and/or flow rate within subject circuit (126, 190) is done by flow generator 150.

In some embodiments, controller 160 may be configured to periodically open gas valve 142 for predetermined "pulses." During pulse delivery, a "bolus" of oxygen is delivered to the subject, e.g., gas valve 142 is opened for predetermined pulse duration, and thereafter closed until the next bolus is to be delivered. In some embodiments, controller 160 may open gas valve 142 for continuous delivery, e.g., throttling gas valve 142 to adjust the flow rate to the subject. In some embodiments, controller 160 may periodically open and throttle gas valve 142 for a predetermined time to vary the volume of the bolus delivered. For example, in some embodiments, controller 160 may have a predetermined and/or a set target flow rate stored in memory. The target flow rate may be provided and may be changed by the user using a user interface (not shown in FIG. 1 or FIG. 2). The target flow rate may be a volume flow rate in units of liter per minute (L/min). For example, system 100 may provide a flow rate of up to about 220 L/min. In some embodiments, system 100 may provide a flow rate between about 30 and 220. In some embodiments, system 100 may provide a flow rate between about 40 and 60 L/min. If the measured flow rate is below the target flow rate, controller 160 controls the gas valve 142 so as to increase the flow rate to the desired or target flow rate. Similarly, if the measured flow rate is above the target flow rate, controller 160 controls the gas valve 142 so as to decrease the flow rate to the desired or target flow rate.

Flow generator 150 is configured to receive the breathable gas from product tank 140 and elevate the flow of the breathable gas to a desired value or range for delivery to the subject. In some embodiments, flow generator 150 may be a blower, a pump, a piston, bellows, and/or other flow generators. For example, flow generator 150 may be a blower that is driven at a substantially constant speed to provide the breathable gas with a substantially constant elevated pressure and/or flow rate. In some embodiments, flow generator 150 may be configured to generate an additional flow of breathable gas (e.g., from a turbine generator and/or from a piston driven breathable gas source) to be used to augment the breathable gas flow to create a breathable gas (e.g., oxygen and air admixture) at a higher flow rate than the breathable gas provided from product tank 140 alone. In some embodiments, the flow rate for delivery to the subject may be equal or greater than 30 L/min and equal or less than 220 L/min, and/or have other ranges.

In some embodiments, flow generator 150 includes a pressure/flow sensor configured to generate output signals indicative of pressure and/or flow associated with the breathable gas in subject circuit (126, 190). In these embodiments, the flow of breathable gas output from control valve 142 is delivered to the pressure/flow sensor in flow generator 150, which outputs a signal indicative of the rate of flow of gas in subject circuit (126, 190). This signal may be used to control flow generator (e.g., speed) 150 to produce a desired flow of breathable gas. For example, if the flow sensor indicates that flow is lower than a threshold value, flow generator 150 may be controlled such that additional flow of breathable gas is supplied to the breathable gas for delivery to the subject. In some embodiments, if the flow of breathable gas provided from product tank 140 is at the desired value and/or in the target range, flow generator 150 may be controlled such that it does not provide additional flow of breathable gas. In some embodiments, system 100 does not include flow generator 150. Instead, flow of the breathable gas is controlled by control valve 142.

In some embodiments, humidifier 136 is configured to humidify the breathable gas for delivery to the subject. In some embodiments, humidifier 136 is distal from the oxygen concentrator 110. In some embodiments, humidifier 136 is proximal to subject interface 190 (for example, humidifier 136 may be an integral part of subject interface 190). In some embodiments, humidifier 136 may be located in other locations within system 100. In some embodiments, humidifier 136 is a discrete component of system 100 (e.g., which can be attached and/or detached from system 100). In some embodiments, humidifier 136 is operatively connected to water reservoir 130 via a water conduit 134. In some embodiments, water conduit 134 includes a water valve 132 between water reservoir 130 and humidifier 136. The water valve is configured to control flow of water from water reservoir 130. The humidifier is configured to receive water from water reservoir 130 and provide humidification of the breathable gas at the subject interface.

In some embodiments, operations of humidifier 136 may be controlled by controller 160 based on output signals from the one or more sensors 180 and/or other information. In other words, humidifier 136 is turned ON and/or OFF based on the signals from the sensors. For example, in some embodiments, in response to receiving a signal from the one or more sensors 180 indicating the start of an inspiration, controller 160 opens water valve 132 to allow a flow of water from a reservoir tank 130 to the humidifier 136. The controller closes valve 132 after receiving a signal from the one or more sensors 180 indicating the beginning of expiration. In some embodiments, controller 160 may control operations of water valve 132 such that opening or closing of water valve 132 is gradual based on the subject breathing cycle (e.g., beginning of inhalation, peak, beginning of exhalation, etc.). In other examples, controller 160 may turn the humidifier ON or OFF at the humidifier level (e.g., by controlling a sub controller in the humidifier) regardless (or in combination) of the position of the water valve 132.

Figure 3:
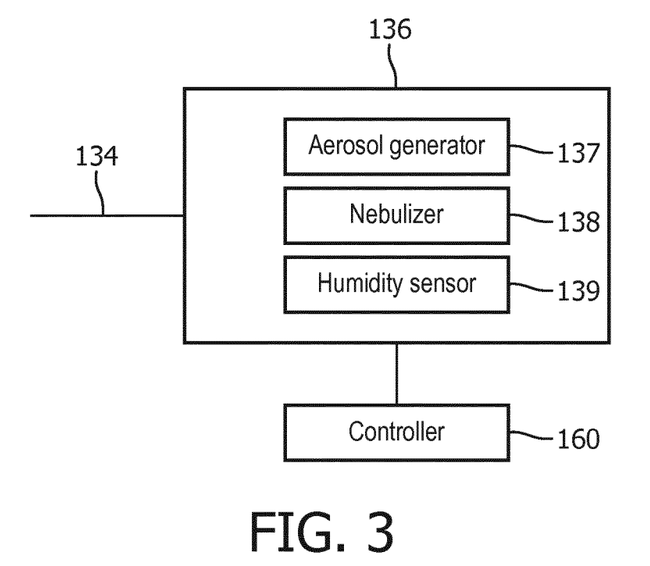
FIG. 3 illustrates an example of features of the system in accordance with one or more implementations.

In some embodiments, humidifier 136 includes an aerosol generator 137 operatively coupled to water reservoir 130 via water conduit 134 (as shown in FIG. 3). Aerosol generator 137 is configured to provide a water vapor to subject interface 190 via water conduit 134 to humidify the flow of breathable gas for delivery to the subject.

In some embodiments, humidifier 136 includes a nebulizer 138 (as shown in FIG. 3) configured to receive water from water reservoir 130 and provide droplets of water to humidify the breathable gas in the subject interface 190. A plurality of suitable nebulizers may be used, for example, mechanical nebulizers, electric nebulizers, jet nebulizers, ultrasonic nebulizers, piezoelectric nebulizers, vibrating mesh technology (VMT) nebulizers, or other types of nebulizers.

In some cases, humidifier 136 includes a heating element configured to heat water received from water reservoir 130 through water line 134 and produce a vapor that is directed to the subject interface 190 (or in some cases, the vapor is produced in the subject interface 190). The vapor produced by humidifier 136 is then added to (or mixed with) the breathable gas being delivered to the subject). In some cases, humidifier 136 may be a nebulizer 138 having a heating element that is configured to heat the droplets of water before misting them into the subject interface 190.

In some embodiments, humidifier 136 may include a humidity sensor 139 (as shown in FIG. 3) configured to measure humidity within humidifier 136 or anywhere downstream from the humidifier (e.g., in subject interface 190). Humidity sensor 139 may be configured to measure absolute, relative, and/or specific humidity. In some embodiments, humidity sensor 139 may be used in combination with a temperature sensor, a flow sensor, and/or a pressure to determine the humidity level (e.g., determined with controller 160). Measurement of humidity may be used to control one or more parameters of the humidifier (e.g., controlled with controller 160). For example, operations of the nebulizer may be controlled to produce a desired level of humidity. For example, when humidifier 136 includes a heating element, the heating element may be controlled so that the vapor produces a threshold level of humidity.

Exhalation valve 170 is operatively coupled to subject interface 190 and is configured to exhaust expired gas from the subject during expiration. Exhalation valve 170 may be located relatively close to the subject interface 190 to minimize dead space in some embodiments (e.g., on or proximal to subject interface 190). It is to be understood, however, that the exhalation valve may be provided at other locations, including providing more than one exhalation valve in subject circuit (126, 190). In some embodiments, exhalation valve 170 is an active exhaust port that may be configured with one or more different configurations (e.g., completely or partially open, and/or completely or partially closed) to control the rate of exhaust from the subject interface to ambient air depending on its configuration. Exhalation valve 170 may eliminate $CO_2$ rebreathing by the subject, since the exhalation gas is released directly in the ambient air. Exhalation valve 170 may allow for relatively small diameter tube (e.g., equal or less than 8 mm) to be used since the subject will not be required to exhale through the resistive load of the small diameter tube.

In some embodiments, controller 160 is configured to control operations of exhalation valve 170 based on one or more parameters. For example, controller 160 may open exhalation valve 170 in response to signals from sensors 180 indicating a start of an exhalation. Responsive to receiving signals indicating a start of an inhalation, the controller closes exhalation valve 170. In some embodiments, exhalation valve 170 may be controlled based on pressure within the subject circuit (126, 190) (e.g., to maintain pressure within a threshold range). Exhalation valve 170 may have different position (e.g., open or closed to various degrees) to control the expiratory pressure. In some embodiments, exhalation valve 170 may include a plurality of orifices configured to release expired gas into ambient air. In these embodiments, the orifices may be controlled individually (opened, or closed) to control the expiratory pressure of the expired gas. In some embodiments, exhalation valve 170 may be a flap valve that opens with exhalation and closes with inhalation.

In some embodiments, exhalation valve 170 may be a passive exhalation valve in the form of a continuously open port that imposes a flow restriction on the exhaust gas to permit control of the pressure of gas within the subject interface assembly 190, including providing positive end expiratory pressure (PEEP) to the subject. It is to be understood that other configurations for the exhalation valve are possible including any that of any conventional port.

In some embodiments (shown in FIG. 2), system 100 includes a valve 152 configured to control operations of flow generator 150 based indications of a start of an exhalation/or exhalation. For example, during exhalation, the expiratory positive airway pressure (EPAP) may be set (or controlled) by closing valve 152 (either completely or partially), and operating valve 170 to control the amount of exhaust from subject to atmosphere. Controlling operation of valve 170 may be done pneumatically based on pressure within patient circuit (126, 190), for example. By completely blocking the flow from the flow generator using valve 152 and/or by ensuring the flow out of valve 170 is greater than the flow through valve 152, the subject does not exhale against any pressure provided by flow generator 150. In some embodiments, valve 152 and gas valve 142 are closed in response to a start of an exhalation (e.g., to completely block flow of gas to the subject), and valve 170 is operated (opened completely or partially) to exhaust gas from the subject to ambient air, thereby controlling expiratory positive airway pressure. In some embodiments, valve 152 and gas valve 142 are controlled such that the flow out of valve 170 is greater than the flow of gas provided to the subject (e.g., by partially or completely closing one or both valves). Other combinations of control of valves 142, 152, and 170 are contemplated.

Sensors 180 are configured to generate output signals conveying information related to one or more parameters of the gas within system 100. The one or more parameters of the gas within system 100 comprise gas parameters related to the pressurized flow of breathable gas, breathing parameters related to respiration of the subject, and/or other parameters. Sensors 180 may comprise one or more sensors that measure such parameters directly (e.g., through fluid communication with the flow of gas in subject circuit (126, 190)). For example, in some embodiments, sensors 180 may include one or more of a spirometer, a pneumotach, variable orifice transducer, differential pressure transducer, a flow transducer, a microphone, an accelerometer, or other conventional sensor devices. In some cases, sensors 180 may comprise one or more sensors that generate output signals related to the one or more parameters indirectly. For example, sensors 180 may comprise one or more sensors configured to generate an output based on an operating parameter of pressure generator 150 (e.g., subject flow and/or pressure estimations from motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, and/or other gas parameters. Breathing parameters related to the respiration of the subject may comprise a tidal volume, an expiratory flow limitation, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters.

Although sensors 180 are illustrated at a single location in system 100, this is not intended to be limiting. Sensors 180 may comprise sensors disposed in a plurality of locations within system 100, such as for example, at various locations within pressure generator 150, within (or in communication with) subject circuit (126, 190), and/or other locations.

Controller 160 includes one or more hardware components and/or software components that control one or more aspects of the operation of system 100. In some embodiments, controller 160 may be operatively coupled to one or more components of system 100, e.g., concentrator 110, valve 142, flow generator 150, exhalation valve 170, sensors 180, water valve 132, humidifier 136, and/or other components of system 100. In some embodiments, the components may be coupled by one or more wires or other electrical leads capable of receiving and/or transmitting signals between controller 160 and the components. In some embodiments, connections between controller 160 and different components of system 100 may be wireless.

In some embodiments, controller 160 may include one or more electrical circuit boards that include a plurality of electrical components including one or more processors, memory, switches, fans, battery chargers, and the like (not shown) mounted to the circuit boards. It will be appreciated that controller 160 may be provided as multiple sub controllers that control different aspects of the operation of system 100. For example, a first sub controller may control operation of concentrator 110 and the sequence of opening and closing of valves 114, e.g., to charge and purge sieve beds 112 in a desired manner. Other sub controllers may be used to control different components of system 100 (e.g., flow generator 150, humidifier 136, valves 132, 142, and 170, and/or other components).

In some embodiments, controller 160 may also be coupled to a user interface (not shown), which may include one or more displays and/or input devices. The user interface may be configured to provide an interface between system 100 and the subject, and/or other users through which the subject and/or other users may provide information to and receive information from system 100. Other users may comprise, for example, a caregiver, a doctor, and/or other users. This enables data, cues, results, and/or instructions and any other communicable items, collectively referred to as "information," to be communicated between a user (e.g., the subject) and one or more components of system 100 and/or allow the user to change the parameters, e.g., turn system 100 on and off, change dose setting or desired flow rate, etc.

Examples of interface devices suitable for inclusion in the user interface comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, the user interface comprises a plurality of separate interfaces. It is to be understood that other communication techniques, either hard-wired or wireless, are also contemplated by the present disclosure as the user interface. For example, the present disclosure contemplates that the user interface may be integrated with a removable storage interface. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as the user interface comprise, but are not limited to, an RS-232 port, RF link, an IR link, modem (telephone, cable or other). In short, any technique for communicating information with system 100 is contemplated by the present disclosure as the user interface.

Subject interface 190 may comprise any type of suitable subject interface 190 for directing a flow of gas toward and/or into a subject's airway (e.g., full face mask, nasal mask, total face mask, nasal pillows mask, nasal cannula, intubation tube, or other interface that communicate a flow of gas with an airway of a subject). The present disclosure is not limited to these examples, and contemplates delivery of the flow of gas to the subject using any interface appliance.

Figure 4:
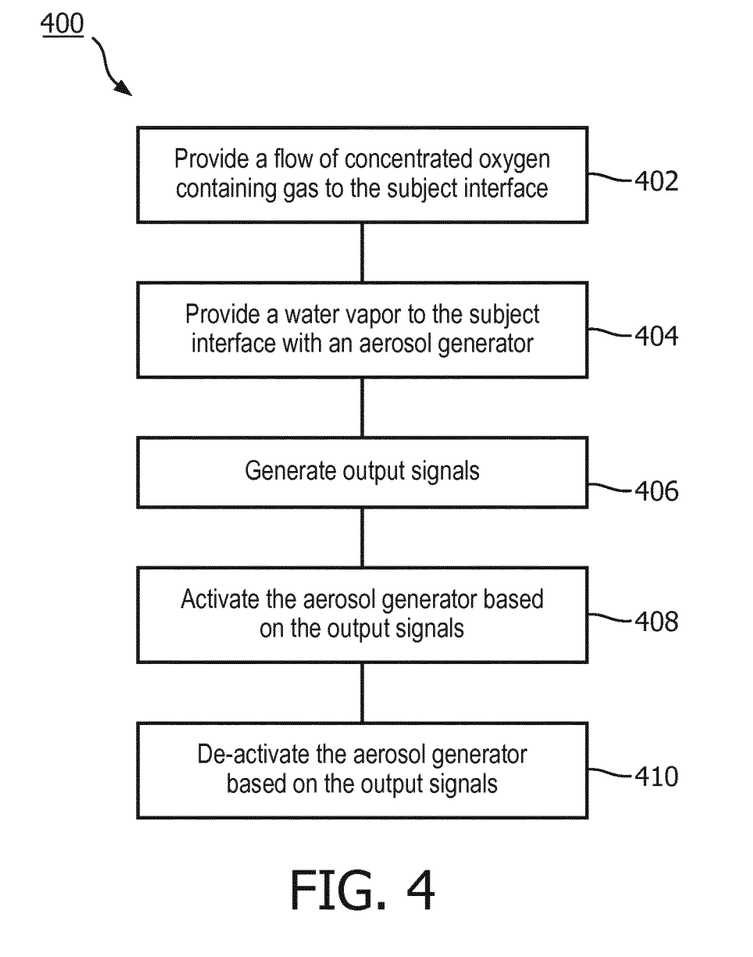
FIG. 4 illustrates an example diagram of operations of the system in accordance with one or more implementations.

FIG. 4 illustrates a method 400 for delivering a humidified flow of concentrated oxygen containing gas to a subject with a system comprising a subject interface, an oxygen concentrator operatively coupled to the subject interface via a first conduit, and an aerosol generator operatively coupled to a water supply via a second conduit. The operations of method 300 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

At an operation 402, a flow of concentrated oxygen containing gas is provided to the subject interface via the first conduit. In some embodiments, the flow of concentrated oxygen containing gas is provided with the oxygen concentrator operatively coupled to the subject interface. In some embodiments, operation 402 is performed by an oxygen concentrator the same as or similar to oxygen concentrator 110 (shown in FIG. 1 and described herein).

At an operation 404, a water vapor is provided to the subject interface via the second conduit to humidify the flow of concentrated oxygen containing gas for delivery to the subject. In some embodiments, the water vapor is provided with the aerosol generator. In some embodiments, operation 404 is performed by an aerosol generator the same as or similar to aerosol generator 137 (described herein).

At an operation 406, one or more output signals conveying information related to one or more parameters of the concentrated oxygen containing gas are generated with one or more sensors. In some embodiments, operation 406 is performed by sensors the same as or similar to sensors 180 (shown in FIG. 1 and described herein.).

At an operation 408, the aerosol generator is activated with a controller responsive to the one or more parameters indicating a start of an inspiration. In some embodiments, operation 408 is performed by a controller the same as or similar to controller 160 (shown in FIG. 1 and described herein.).

At an operation 410, the aerosol generator is de-activated with the controller responsive to the one or more parameters indicating a start of an expiration. In some embodiments, operation 410 is performed by a controller the same as or similar to controller 160 (shown in FIG. 1 and described herein.).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for delivering a humidified flow of concentrated oxygen containing gas to a subject having a mouth and nares, the system comprising:
    a subject interface structured to engage the mouth and/or nares of the subject;
    an oxygen concentrator operatively coupled to the subject interface via a first control valve and a first conduit, the oxygen concentrator configured to provide a flow of concentrated oxygen containing gas to the subject interface via the first conduit;
    a flow generator operatively coupled to the first conduit between the first control valve and the subject interface via a second control valve;
    an aerosol generator operatively coupled to a water supply via a second conduit, the aerosol generator configured to provide a water vapor to the subject interface to humidify the flow of concentrated oxygen containing gas at the subject interface;
    an exhalation valve operatively coupled to the subject interface, the exhalation valve configured to control an expiratory pressure of gas expired by the subject;
    one or more sensors configured to generate output signals that convey information related to one or more parameters of the concentrated oxygen containing gas; and
    a controller configured to:
        activate the aerosol generator responsive to the one or more parameters indicating a start of an inspiration, and de-activate the aerosol generator responsive to the one or more parameters indicating a start of an expiration;
        control operations of the exhalation valve such that the exhalation valve is opened responsive to the one or more parameters indicating a start of an expiration, and the exhalation valve is closed responsive to the one or more parameters indicating a start of an inspiration; and
        control operations of the first control valve to provide a controlled pressure and/or flow of breathable gas to the subject.

2. The system of claim 1, wherein at least portions the first conduit and the second conduit are included in a multi-lumen tube.

3. The system of claim 2, wherein the multi-lumen tube has an internal diameter of less than 8 millimeters.

4. The system of claim 1, wherein the one more sensors are further configured to generate output signals that convey information related to humidity within the subject interface, and wherein the controller is further configured to control operations of the aerosol generator based on the humidity within the subject interface.

5. The system of claim 1, wherein the controller is further configured to control operation of the second control valve to provide the controlled pressure and/or flow of the breathable gas to the subject.

6. The system of claim 1, wherein the aerosol generator is provided as an integral part of the subject interface.

7. A method for delivering a humidified flow of concentrated oxygen containing gas to a subject having a mouth and nares, the method comprising:
    providing, with an oxygen concentrator operatively coupled to a subject interface structured to engage the mouth and/or nares of the subject, a flow of concentrated oxygen containing gas to the subject interface via a first conduit;
    providing, with an aerosol generator provided as an integral part of the subject interface and operatively coupled to a water supply via a second conduit, a water vapor to the subject interface to humidify the flow of concentrated oxygen containing gas at the subject interface;
    controlling, with an exhalation valve operatively coupled to the subject interface, an expiratory pressure of gas expired by the subject;
    controlling, with a first control valve positioned between the oxygen concentrator and the subject interface, the flow of concentrated oxygen containing gas to the subject interface;
    generating, with one or more sensors, output signals that convey information related to one or more parameters of the concentrated oxygen containing gas;
    activating, with a controller, the aerosol generator responsive to the one or more parameters indicating a start of an inspiration, and de-activate the aerosol generator responsive to the one or more parameters indicating a start of an expiration;
    controlling, with the controller, operations of the exhalation valve such that the exhalation valve is opened responsive to the one or more parameters indicating a start of an expiration, and the exhalation valve is closed responsive to the one or more parameters indicating a start of an inspiration; and
    controlling, with the controller, operations of the first control valve so as to provide a controlled pressure and/or flow of breathable gas to the subject.

8. The method of claim 7, wherein the humidified flow of concentrated oxygen containing gas is delivered to the subject with a multi-lumen tube, and wherein at least portions of the first conduit and the second conduit are included in the multi-lumen tube.

9. The method of claim 7, further comprising:
    generating, with the one or more sensors, output signals that convey information related to humidity within the subject interface, wherein the controller is further configured to control operations of the aerosol generator based on the humidity within the subject interface.

10. The method of claim 7, further comprising:
    providing, with a flow generator operatively coupled to the first conduit between the first control valve and the subject interface, a flow of gas to the first conduit;

controlling, with a second control valve positioned between the flow generator and the first conduit, the flow of gas to the first conduit; and controlling, with the controller, operations of the second control valve so as to provide the controlled pressure and/or flow of the breathable gas to the subject.

\* \* \* \* \*